United States Patent
Michel et al.

(12)

(10) Patent No.: US 6,759,396 B1
(45) Date of Patent: *Jul. 6, 2004

(54) COMPOSITIONS BASED ON A SYNERGISTIC MIXTURE OF AT LEAST ONE VDR LIGAND AND A RETINOID

(75) Inventors: Serge Michel, Roquefort-les-Pins (FR); Veronique Dionisius-Pouget, Valbonne (FR)

(73) Assignee: Centre International de Recherches Dermatalogiques Galderma (C.I.R.D.) Galderma, Valbonne (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,695
(22) PCT Filed: Sep. 10, 1996
(86) PCT No.: PCT/FR96/01386
§ 371 (c)(1), (2), (4) Date: Jul. 11, 1997
(87) PCT Pub. No.: WO97/09987
PCT Pub. Date: Mar. 20, 1997

(30) Foreign Application Priority Data

Sep. 15, 1995 (FR) .............................. 95 10854

(51) Int. Cl.⁷ ................... A61K 31/07; A61K 31/203; A61K 31/19; A61K 31/59
(52) U.S. Cl. .................. 514/167; 514/569; 514/828
(58) Field of Search ................. 514/167, 569, 514/828

(56) References Cited

U.S. PATENT DOCUMENTS 4,717,720 A * 1/1988 Shroot et al. ............ 514/63
5,716,624 A   2/1998 Bernardon
5,780,676 A * 7/1998 Boehm et al. ............ 562/490
5,952,382 A * 9/1999 Bernardon ................ 514/569

FOREIGN PATENT DOCUMENTS

EP          0658553   *  6/1995
EP           661258       7/1995

OTHER PUBLICATIONS

Majewski et al. (1993) Cancer Letters 75: 35–39, 1993.*
R. Trafna, et al., "Biologic Basis of Retinoids and Vitamin D3 Action in Proliferative Skin Diseases", *The Dermatological Clinic of the Warsaw Medical Academy*, 1994, pp. 573–578 (English language abstract enclosed).
S. Majewski et al., "Retinoids and 1,25–Dihydrodxyvitamin D3 (VD3) Synergistically Inhibit Angiogenic Potential of Human Transformed Epithelial Cell Lines", *Journal of Investigative Dermatology*, 1995, p. 604.
W. Bollag et al., "Cancer Combination Chemotherapy with Retinoids: Experimental Rationale", *Leukemia (Basingstoke)*, 1994, pp. 11–15.
S. Majewski et al., "Inhibition of Tumor Cell–Induced Angiogenesis by Retinoids, 1,25–Dihydroxyvitamin D–3 and their Combination", *Cancer Letters*, 1993, pp. 35–39.

* cited by examiner

*Primary Examiner*—Michael Pak
(74) *Attorney, Agent, or Firm*—Burns, Doane, Swecker & Mathis, L.L.P.

(57) ABSTRACT

A novel combination of one or more ligands with VDR receptor selective activity and one or more retinoids selective for RARγ receptors as opposed to RARα receptors is described, as well as the use thereof in cosmetic and skin-care applications for treating disorders related to a hyperproliferation of cells, in particular skin cells, such as psoriasis.

19 Claims, 2 Drawing Sheets

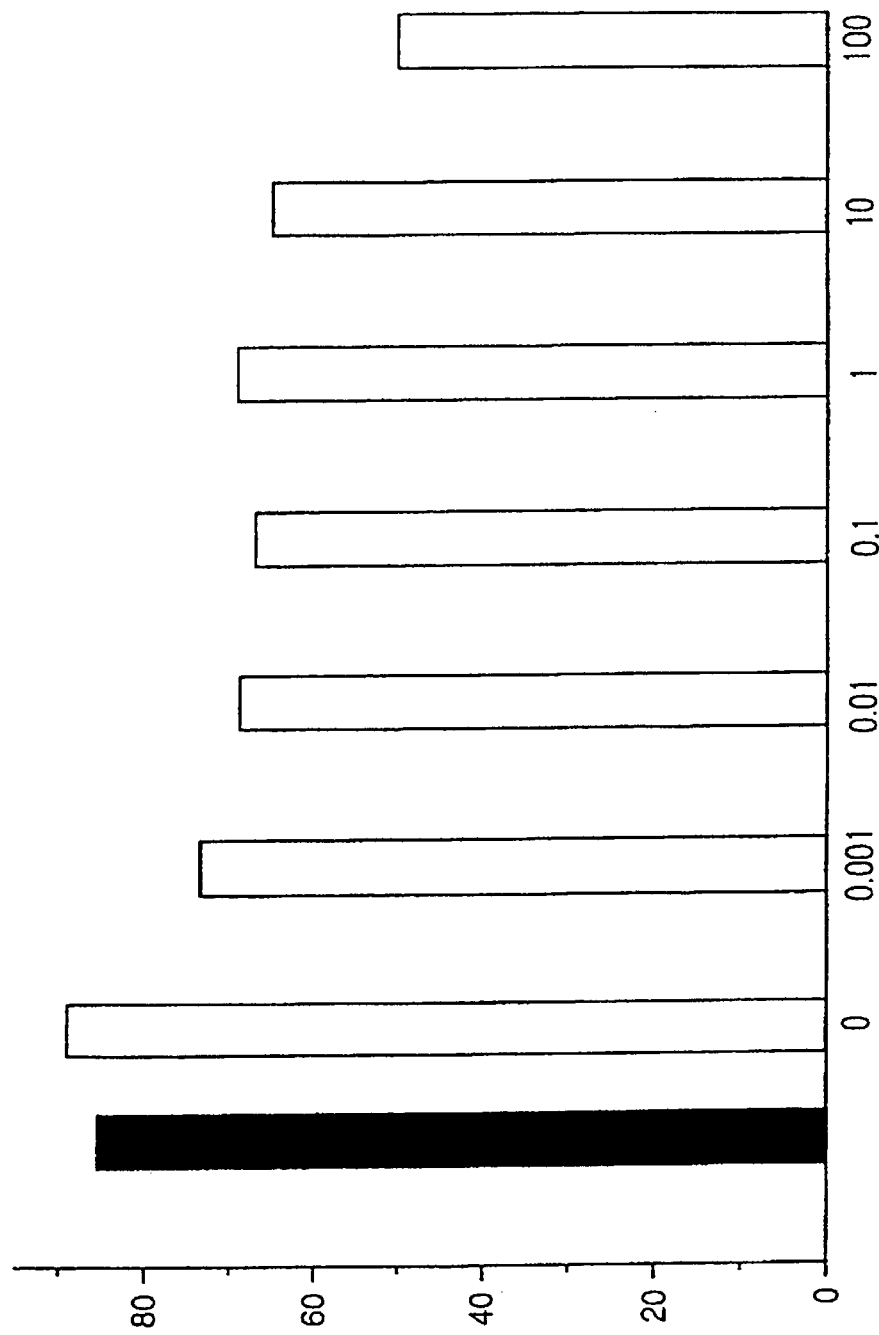

COMPOSITIONS BASED ON A SYNERGISTIC MIXTURE OF AT LEAST ONE VDR LIGAND AND A RETINOID

This application is a national stage filing under 35 U.S.C. §371 of International Application No. PCT/FR96/01386 filed on Sep. 10, 1996, which International Application was published by the International Bureau in English on Mar. 20, 1997.

The invention relates to a novel composition, in particular a pharmaceutical composition, comprising a synergistic combination of at least one ligand having activity for nuclear receptors of VDR type and at least one specific retinoid, as well as to the use of this composition in the pharmaceutical or cosmetic field.

It is known that a ligand having activity for nuclear receptors of VDR (vitamin D3 receptor) type, such as 1α,25-dihydroxyvitamin D3 or analogues thereof, inhibits the proliferation of keratinocytes. Thus, this type of compound is used to treat psoriasis. However, these compounds, such as 1α,25-dihydroxyvitamin D3, have side-effects: hypercalcaemia or hypercalciuria, due to an increase in the level of calcium in the serum.

It is known that retinoic acid is a modulator (i.e. an inhibitor or, on the contrary, a stimulator, depending on the nature of the cells treated) of the differentiation and/or proliferation of many normal or transformed cell types. For example, it inhibits the differentiation of epithelial cells, such as epidermal keratinocytes, without being especially active on the proliferation of these cells. It also inhibits the proliferation of many transformed cells, such as melanoma cells.

It is known, in general, that all-trans retinoic acid acts on the differentiation and/or proliferation of cells by interacting with nuclear receptors or RARs (retinoic acid receptors) contained in the cell nucleus. Many synthetic structural analogues of all-trans retinoic acid or of 9-cis-retinoic acid, commonly known as "retinoids", have been described to date in the literature. There exists, at the present time, three identified subtypes of RAR receptors referred to respectively as RAR-α, RAR-β and RAR-γ. After binding of the ligand (i.e. of the all-trans retinoic acid), these receptors interact with the promoter region of genes regulated by retinoic acid at the level of specific response elements (RARE).

Certain analogues may bind and activate a specific subtype of RAR (α, β or γ) receptor. Other analogues, lastly, have no specific selective activity towards these various receptors. In this respect, and, for example, all-trans retinoic acid activates RARs (specific RAR agonist ligand), all subtypes being taken together, whereas 13-cis retinoic acid does not bind to the α or γ receptors.

Some of these retinoids have already been combined with vitamin D derivatives. Thus, in patent application AU-A-37161/93, 9-cis- or 13-cis-retinoic acid is combined with vitamin D derivatives. However; these combinations prove to be relatively unsatisfactory, in particular in the treatment of psoriasis. The need to find specific combinations which are of noteworthy efficacy, in particular in the treatment of psoriasis, may thus be appreciated.

One of the aims of the present invention is thus to be able to make available a novel product which exhibits appreciable inhibition of cell proliferation, in particular of skin cells, and more particularly of keratinocytes, allowing this product to be used in the treatment of disorders associated with cell hyperproliferation, in particular dermatological disorders associated with cell hyperproliferation.

Another aim of the present invention is to be able to make available a medicinal product which reduces, or even does away altogether with, the side-effects of ligands having activity for nuclear receptors of VDR type.

The Applicant has just discovered that the combination, which is novel per se, and in particular as a medicinal product, of at least one ligand having activity for nuclear receptors of VDR type and a specific retinoid which is selective for RARγ receptors relative to RARα receptors, makes it possible to inhibit the proliferation of keratinocytes in an entirely noteworthy manner. This result is all the more unexpected and surprising since these retinoids, when they are used alone, have no, or substantially no, intrinsic antiproliferative activity towards these same cells.

This discovery forms the basis of the present invention.

Given the noteworthy activities which this combination in accordance with the invention exhibits towards keratinocytes, it naturally finds a preferred application in the treatment of dermatological disorders associated with hyperproliferation of skin cells, and more particularly of keratinocytes.

Thus, in one of its first aspects, the subject of the present invention is a combination product consisting of the combination of at least one ligand having activity for nuclear receptors of VDR type and at least one retinoid which is selective for RARγ receptors relative to RARα receptors.

In a general and qualitative manner, a given substance (or ligand) is said to be specific for a particular receptor when the said substance exhibits an affinity for the said particular receptor which is stronger than that which it exhibits elsewhere for the other receptors.

The dissociation constants are determined by means of tests which are standard to those skilled in the art. These tests are described in particular in the following references: (1) "Selective Synthetic Ligands for Nuclear Retinoic Acid Receptor Subtypes" in RETINOIDS, Progress in Research and Clinical Applications, Chapter 19 (pp 261–267), Marcel Dekker Inc., published by Maria A. Livrea and Lester Packer; (2) "Synthetic Retinoids: Receptor Selectivity and Biological Activity" in Pharmacol. Skin, Basle, Karger, 1993, Volume 5, pp. 117–127; (3) "Selective Synthetic Ligands for Human Nuclear Retinoic Acid Receptors" in Skin Pharmacology, 1992, Vol. 5, pp. 57–65; (4) "Identification of Synthetic Retinoids with Selectivity for Human Nuclear Retinoic Acid Receptor-γ" in Biochemical and Biophysical Research Communications, Vol. 186, No. 2, July 1992, pp. 977–983; (5) "Selective High Affinity RAR-α or RAR-β Retinoic Acid Receptor Ligands" in Mol. Pharmacol., Vol. 40, pp. 556–562.

In an advantageous manner, the retinoids which are selective for the RARγ receptors relative to the RARα receptors have an RARα/RARγ dissociation constant ratio greater than or equal to 8.

Among the retinoids which are selective for the RARγ receptors relative to the RARα receptors, mention may be made in particular of 6-[3-(1-adamantyl)-4-hydroxyphenyl]-2-naphthoic acid (RARα/RARγ=8.5), 6-[3-(1-adamantyl)-4-methoxyphenyl]-2-naphthoic acid (RARα/RARγ=84.4) and 2-hydroxy-4-[3-hydroxy-3-(5,6,7,8-tetrahydro-5,5,8,8-tetramethyl-2-naphthyl)-1-propynyl]benzoic acid (RARα/RARγ=36.6) or derivatives thereof.

In general, the weight ratio between at least one ligand having activity for nuclear receptors of VDR type and at least one retinoid which is selective for RARγ receptors relative to RARα receptors is between 1/1000 and 1000/1. Preferably, this weight ratio is between 1/10 and 10/1.

The subject of the present invention is also a novel composition, in particular a pharmaceutical composition, characterized in that it comprises, in a physiologically acceptable support, a combination product as defined above.

The ligands having activity for the VDR receptor are used for the treatment of osteoporosis, and it may thus be envisaged to use this combination product according to the invention for the treatment of osteoporosis.

However, this combination product proves to be very advantageous for a treatment intended to inhibit cell proliferation, in particular the proliferation of skin cells, and more particularly of keratinocytes, in particular for the treatment of psoriasis.

The subject of the invention is thus the use of at least one retinoid which is selective for RARγ receptors relative to RARα receptors, for the manufacture of a pharmaceutical composition intended to increase the inhibitory activity on cell proliferation, in particular on skin cells, more particularly on keratinocytes, due to at least one ligand having activity for the VDR receptor used, for the treatment of disorders associated with cell hyperproliferation, in particular dermatological disorders associated with hyperproliferation of skin cells.

Thus, in the context of this use according to the invention, the retinoid may be administered, in a simultaneous manner or otherwise, via identical or different routes to the administration of the ligand having activity for the VDR receptor.

The present invention thus also relates to a product comprising at least one ligand having activity for nuclear receptors of VDR type and at least one retinoid which is selective for RARγ receptors relative to RARα receptors, as a combination product for simultaneous or separate use or use spread out over time, for the treatment of disorders associated with cell hyperproliferation, in particular dermatological disorders associated with hyperproliferation of skin cells, more particularly of keratinocytes.

In the case where the retinoid is administered simultaneously and thus via an identical route to that of administration of the ligand having activity for the VDR receptor, the subject of the invention, lastly, is the use of the above combination product for the manufacture of a pharmaceutical composition, more particularly a dermatological composition, intended to treat disorders associated with cell hyperproliferation, in particular dermatological disorders associated with hyperproliferation of skin cells, and more particularly of keratinocytes. This composition is more particularly intended for the treatment of psoriasis.

The term skin cells is understood to refer to keratinocytes, melanocytes, fibroblasts, Merkel cells and Langerhans cells.

It will be noted in general that the active doses to be used in order to obtain the desired effect may be low, which constitutes an appreciable advantage when dealing with problems of undesirable side-effects liable to arise in the organisms to be treated or in the course of treatment, such as hypercalcaemia or hypercalciuria.

Other characteristics, aspects, objects and advantages of the invention will become even more clearly apparent on reading the description and the figures which follow, as well as the various specific, but in no way limiting, examples intended to illustrate it.

DESCRIPTION OF THE FIGURES

FIG. 2: Effect of the combination of 1,25-dihydroxyvitamin D3 and compound 1 on the inhibition of keratinocyte proliferation. The results are expressed as a percentage of keratinocyte proliferation relative to a control (DMSO) as a function of the concentration expressed in nM of compound 1 in the presence of 1 nM of 1,25-dihydroxyvitamin D3 (□). In this figure, the value of compound 1 alone at 100 nM (■) is also given.

Figure 1:
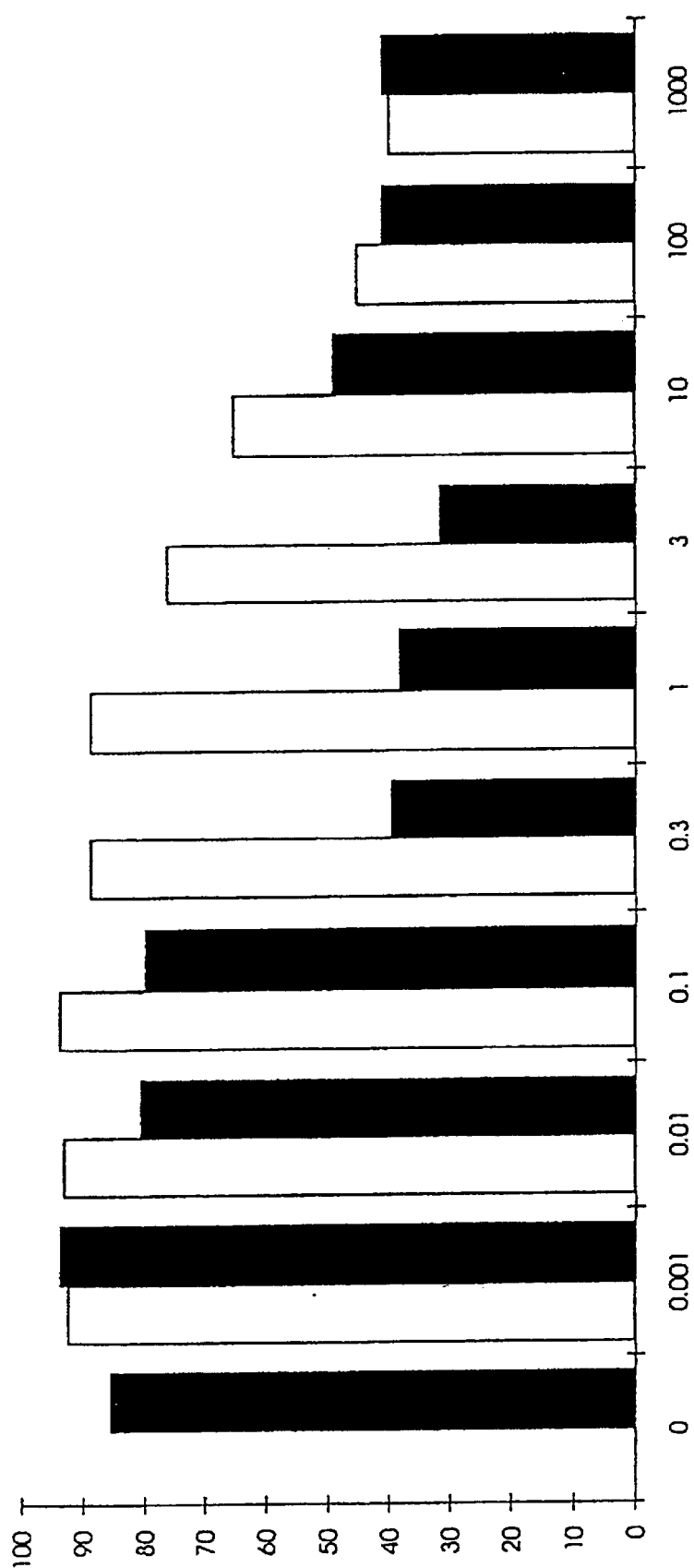
FIG. 1: Effect of the combination of 1,25-dihydroxyvitamin D3 and compound 1 (=6-[3-(1-adamantyl)-4-hydroxyphenyl]-2-naphthoic acid) on the inhibition of keratinocyte proliferation. The results are expressed as a percentage of keratinocyte proliferation relative to a control (DMSO) as a function of the concentration expressed in nM of 1,25-dihydroxyvitamin D3 in the absence (□) or in the presence (■) of compound 1 at a concentration of 100 nM.

6-[3-(1-Adamantyl)-4-hydroxyphenyl]-2-naphthoic acid and 6-[3-(1-adamantyl)-4-methoxyphenyl]-2-naphthoic acid have already been described in U.S. Pat. No. 4,717,720. 2-Hydroxy-4-[3-hydroxy-3-(5,6,7,8-tetrahydro-5,5,8,8-tetramethyl-2-naphthyl)-1-propynyl]-benzoic acid is described in patent application EP 661,258. Their derivatives may correspond to their esters, their amides, their salts, their alcohols or their aldehydes.

Among the ligands having activity for the VDR receptor, mention may be made of the following compounds:

vitamin D3 (cholecalciferol), vitamin D2 (ergocalciferol), calcipotriol (or calcipotriene), sold in particular by the company Leo under the trade name Daivonex®, 25-hydroxyvitamin D3, 1α-hydroxyvitamin D3, 1α,25-dihydroxyvitamin D3 (calcitriol), 1α,25,26-trihydroxyvitamin D3, 1α,23,25-trihydroxyvitamin D3, 24,25-dihydroxyvitamin D3, 1α,25-dihydroxyvitamin D2, 1α-hydroxyvitamin D2, 1α,24-dihydroxyvitamin D2, 1α,24-dihydroxyvitamin D3 (tacalcitol), (5Z, 7E, 23S)-26,26,26,27,27,27-hexafluoro-9,10-secocholesta-5,7,10(19)-triene-1α-3β,23,25-tetraol, 26,26,26,27,27,27-hexafluoro-9,10-secocholesta-5,7,10 (19)-triene-1α,25-diol (26,26,26,27,27,27-hexafluoro-1α,25-dihydroxy-vitamin D3), or the vitamin D derivatives described in patent application WO 96/22776.

It is preferred to use 1α,25-dihydroxyvitamin D3.

In the following text, the term topical route is understood to refer to any technique of administration of a product by direct application thereof to a surface (or external) part of the body, such as the skin or the mucous membranes, and the term systemic route is understood to refer to any technique of administration of a product via a route other than topical, for example oral, enteral and/or parenteral.

The subject of the present invention is thus, inter alia, a novel pharmaceutical composition intended in particular for treating the skin, characterized in that it comprises, in a physiologically acceptable support which is compatible with the mode of administration selected for this composition, at least one ligand having activity for the VDR receptor and at least one retinoid which is selective for RARγ receptors relative to RARα receptors, as active principles.

The administration of the active agents (retinoid or ligand having activity for the VDR receptor) or of the combination according to the invention may be carried out via the enteral, parenteral, topical or ocular route. However, the compositions (or combinations) according to the invention are preferably packaged in a form which is suitable for topical application.

Via the enteral route, the compositions may be in the form of tablets, gelatin capsules, coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

The active agent mixtures in accordance with the invention are generally administered at daily doses of approximately from 0.01 mg/kg to 100 mg/kg of body weight, taken at a rate of 1 to 3 times/day.

Via the topical route, the pharmaceutical compositions, which are therefore more particularly intended for treating the skin, may be in the form of ointments, creams, milks, salves, powders, impregnated pads, solutions, gels, sprays, lotions or suspensions. They may also be in the form of microspheres or nanospheres or lipid vesicles or polymeric vesicles or polymeric patches and hydrogels allowing controlled release of the active agents. These topical-route compositions may moreover be either in anhydrous form or in an aqueous form, depending on the clinical application.

The compositions for topical use in accordance with the invention contain the VDR ligand or ligands at a concentration generally of between 0.001% and 10% by weight, preferably between 0.1 and 1% by weight, relative to the total weight of the composition. Similarly, the compositions for topical use in accordance with the invention contain the retinoid or retinoids at a concentration generally of between 0.001% and 10% by weight, preferably between 0.1 and 1% by weight, relative to the total weight of the composition.

Via the ocular route, they are mainly eye drops.

The compositions according to the invention may, of course, also contain inert or even pharmacodynamically active additives or combinations of these additives, and in particular: wetting agents; depigmenting agents such as hydroquinone, azelaic acid, caffeic acid or kojic acid; emollients; hydrating agents such as glycerol, PEG 400, thiamorpholinone and derivatives thereof or urea; antiseborrhoeic or antiacne agents such as S-carboxymethylcysteine, S-benzylcysteamine, their salts or their derivatives, or benzoyl peroxide; antifungal agents such as ketoconazole or poly(4,5-methylene-3-isothiazolidones); antibacterial agents, carotenoids and, in particular, β-carotene; antipsoriatic agents such as anthraline and derivatives thereof; and, lastly, eicosa-5,8,11,14-tetraynoic acid and eicosa-5,8,11-triynoic acid, and esters and amides thereof.

The compositions according to the invention may also contain flavour enhancers, preserving agents such as parahydroxybenzoic acid esters, stabilizers, humidity regulators, pH regulators, osmotic pressure modifiers, emulsifying agents, UV-A and UV-B screening agents, and antioxidants such as α-tocopherol, butylhydroxyanisole or butylhydroxytoluene.

The dermatological disorders associated with hyperproliferation of skin cells are, in particular, the following:
1) Dermatological complaints linked to a keratinization disorder which has a bearing on cell proliferation, in particular common acne, comedones, polymorphonuclear leukocytes, nodulocystic acne, acne conglobata, senile acne and secondary acne such as solar, medication-related or profession-related acne.
2) Other types of keratinization disorder, in particular ichthyosis, ichthyosiform states, Darier's disease, palmoplantar keratoderma, leucoplasia and leucoplasiform states, and cutaneous or mucous (buccal) lichen.
3) Other dermatological complaints associated with a keratinization disorder with an inflammatory and/or immunoallergic component and, in particular, all forms of psoriasis, whether cutaneous, mucous or ungual psoriasis, and even psoriatic rheumatism, or alternatively cutaneous atopy such as eczema or respiratory atopy, or alternatively gingival hypertrophy.
4) All dermal or epidermal proliferations, whether benign or malignant, and whether of viral origin or otherwise, such as common warts, flat warts and verruciform epidermodysplasia, oral or florid papillomatoses, it being also possible for the proliferations to be induced by ultraviolet radiation, in particular in the case of basocellular and spinocellular epithelioma.
5) For treating other dermatological disorders such as bullosis and collagen diseases.
6) Ageing of the skin, whether this is light-induced or chronological ageing, or for actinic keratoses and pigmentations, or any pathology associated with chronological or actinic ageing.
7) Stigmata of epidermal and/or dermal atrophy induced by local or systemic corticosteroids, or any other form of cutaneous atrophy.
8) Cicatrization disorders or vibices.
9) Disorders of sebaceous functioning such as acneic hyperseborrhoea or simple seborrhoea.
10) Cancerous or precancerous skin states.
11) Any complaint of viral origin on the skin.
12) Dermatological complaints with an immunological component.

The compositions according to the invention prove to be particularly effective for treatments 1) to 4), and more especially for treating all forms of psoriasis.

Several examples intended, on the one hand, to demonstrate the effects associated with the present invention, and, on the other hand, to illustrate various specific formulations in accordance with the invention will now be given, without any limitation being implied.

EXAMPLE 1

The aim of this example is to demonstrate the in vitro activity of the synergistic combination in accordance with the invention on keratinocyte proliferation. The keratinocytes were obtained from a specimen of skin obtained from plastic surgery. They are used at the second passage.

The experimental procedure and the methods for determining the proliferation were as follows:

Culturing of the Keratinocytes

The cells are cultured at 37° C. in a humid atmosphere in the presence of 5% $CO_2$ according to the method of Rheinwald and Green in the presence of 3T3 fibroblasts treated with mitomycin in MEM medium containing 10% (v/v) foetal calf serum (FCS), 0.4 µg/ml of hydrocortisone, 10 ng/ml of EGF (epidermal growth factor) and $10^{-9}$ M chloreratoxin. The 3T3 cells are inoculated 24 h before the keratinocytes at a rate of 15,000 cells per $cm^2$. Next, the keratinocytes are inoculated at a rate of 4000 cells per $cm^2$.

Treatment of the Cells

The cells are treated 2 h after inoculation of the keratinocytes, with compound 1 or 1,25-dihydroxyvitamin D3 diluted in DMSO. The final concentration of DMSO in the culture medium does not exceed 0.2% (v/v). After culturing for 4 days, the cells are harvested in order to determine the proliferation.

Measurement of the Proliferation

The cell proliferation is determined using a kit with the reference name "Cell proliferation kit II" (XTT assay) used according to the indications of the manufacturer (Boehringer, ref. 1465 05). It is expressed in absorbance units at 495 nm. The lower the value of the absorbance measured, the more the keratinocyte proliferation has been inhibited.

The results obtained are collated in FIGS. 1 and 2. These figures quantify the change in the level of keratinocyte proliferation as a function of the concentration of the active agents used.

These figures show clearly that the combination of compound 1 and 1,25-dihydroxyvitamin D3 exhibits very good inhibition on keratinocyte proliferation.

The same experiment was also carried out with a combination of all-trans, 9-cis or 13-cis retinoic acid and 1,25-dihydroxyvitamin D3 under identical conditions. No synergism of inhibition on keratinocyte proliferation is observed.

EXAMPLE 2

In this example, various specific formulations based on combinations in accordance with the invention are illustrated (compound 1 is the one defined above in the description).

A - ORAL ROUTE (a) Composition for a 100 mg soft capsule

| | | |
|---|---|---|
| Compound 1 | | 1.00 mg |
| 1α,25-Dihydroxyvitamin D3 | | 1.00 mg |
| BHT | | 0.01 mg |
| D,L-α-Tocopherol | | 0.05 mg |
| Vegetable oil | qs | 100 mg |

(b) Drinkable suspension in 10 ml ampules

| | | |
|---|---|---|
| Compound 1 | | 0.05 g |
| 1α,25-Dihydroxyvitamin D3 | | 0.05 g |
| Glycerol | | 1.000 g |
| 70% Sorbitol | | 1.000 g |
| Sodium saccharinate | | 0.010 g |
| Methyl para-hydroxybenzoate | | 0.080 g |
| Flavouring | qs | |
| Purified water | qs | 10 ml |

B - TOPICAL ROUTE (a) Ointment

| | |
|---|---|
| Compound 1 | 0.1 g |
| 1α,25-Dihydroxyvitamin D3 | 0.1 g |
| Petrolatum qs 100 | |

(b) Ointment

| | |
|---|---|
| Compound 1 | 0.1 g |
| 1α,25-Dihydroxyvitamin D3 | 0.1 g |
| Isopropyl myristate | 81.520 g |
| Liquid petrolatum | 9.100 g |
| Silica ("Aerosil 200" sold by Degussa) | 9.180 g |

(c) Nonionic water-in-oil cream

| | | |
|---|---|---|
| Compound 1 | | 0.100 g |
| 1α,25-Dihydroxyvitamin D3 | | 0.100 g |
| Mixture of emulsifying lanolin alcohols, waxes and oils ("anhydrous eucerine" sold by BDF) | | 39.900 g |
| Methyl para-hydroxybenzoate | | 0.075 g |
| Propyl para-hydroxybenzoate | | 0.075 g |
| Sterile demineralized water | qs | 100 g |

(d) Lotion

| | |
|---|---|
| Compound 1 | 0.100 g |
| 1α,25-Dihydroxyvitamin D3 | 0.100 g |
| polyethylene glycol (PEG 400) | 69,800 g |
| 95% Ethanol | 30,000 g |

(e) Hydrophobic ointment

| | | |
|---|---|---|
| Compound 1 | | 0.300 g |
| 1α,25-Dihydroxyvitamin D3 | | 0.300 g |
| Isopropyl myristate | | 36.400 g |
| Silicone oil ("Rhodorsil 47 V 300" sold by Rhône-Poulenc) | | 36.400 g |
| Beeswax | | 13.600 g |
| Silicone oil ("DC200" 350 cps sold by Dow Corning) | qs | 100 g |

(f) Nonionic oil-in-water cream

| | | |
|---|---|---|
| Compound 1 | | 0.500 g |
| 1α,25-Dihydroxyvitamin D3 | | 0.500 g |
| Cetyl alcohol | | 4.000 g |
| Glyceryl monostearate | | 2.500 g |
| PEG 50 stearate | | 2.500 g |
| Karite butter | | 9.200 g |
| Propylene glycol | | 2.000 g |
| Methyl para-hydroxybenzoate | | 0.075 g |
| Propyl para-hydroxybenzoate | | 0.075 g |
| Sterile demineralized water | qs | 100 g |

What is claimed is:

1. A composition suitable for the treatment of a disorder involving abnormal skin cell proliferation with comprises the combination of at least one ligand which binds a nuclear receptor of the VDR type, and at least one retinoid which exhibits selective binding affinity for RARγ receptors relative to RARα receptors, wherein said retinoid is selected from the group consisting of 6-[3-(1-adamantyl)-4-hydroxyphenyl]-2-naphthoic acid, 6-[3-(1-adamantyl)-4-methoxyphenyl]-2-naphthoic acid and derivatives thereof, wherein said combination of at said least one ligand which binds to a nuclear receptor of VDR type, and said at least one retinoid which exhibits selective affinity for RARγ receptors relative to RARα receptors exhibits synergistic inhibition of skin cell proliferation relative to either of said ligands.

2. A composition of matter which affects skin cell proliferation which comprises the combination of at least one ligand which binds to a nuclear receptor of the VDR type, and at least one retinoid which exhibits selective binding affinity for RARγ receptors relative to RARα receptors, wherein said retinoid is selected from the group consisting of 6-[3-(1-adamantyl)-4-hydroxyphenyl]-2-naphthoic acid, 6-[3-(1-adamantyl)-4-methoxyphenyl]-2-naphthoic acid, and derivatives thereof wherein said combination of said at least one ligand which binds to a nuclear receptor of VDR type, and said at least one retinoid which exhibits selective affinity for RARγ receptors relative to RARα receptors exhibits synergistic inhibition of skin cell proliferation relative to either of said ligands.

3. The composition according to claim 1, wherein the disorder involving abnormal skin cell proliferation is a dermatological disorder.

4. The composition according to claim 3, wherein said dermatological disorder is associated with skin cell hyperproliferation.

5. A composition according to claim 2, wherein said skin cells are keratinocytes.

6. The composition according to claim 1, wherein the skin cells which abnormally proliferate are selected from the group consisting of keratinocytes, melanocytes, fibroblasts, Merkel cells and Langerhans cells.

7. A composition according to claim 2, wherein the retinoid which exhibits selective binding affinity for RARγ receptors relative to RARα receptors has an RARα/RARγ dissociation constant ratio which exceeds or is equal to 8.

8. A composition according to claim 1, wherein the retinoid which exhibits selective binding affinity for RARγ receptors relative to RARα receptors has an RARα/RARγ dissociation constant ratio which is greater than or equal to 8.

9. A composition according to claim 2, wherein the ligand having activity wherein the ligand which specifically binds to a VDR receptor is selected from the group consisting of vitamin D3, vitamin D2, 25-hydroxyvitamin D3, 1α,25-dihydroxyvitamin D3 (calcitriol), 1α,25,26-trihydroxyvitamin D3, 1α,23,25-trihydroxyvitamin D3, 24,25-dihydroxyvitamin D3, 1α,25-dihydroxyvitamin D2, 1α-hydroxyvitamin D2, 1α,24-dihydroxyvitamin D2, 1α,24-dihydroxyvitamin D3 (tacalcitol), (5Z,7E,23S)-26,26,26,27,27,27-hexafluoro-9,10-secocholesta-5,7,10(19)-triene-1α-3β,23,25-tetraol and 26,26,26,27,27,27-hexafluoro-9,10-secocholesta-5,7,10(19)-triene-1α,25-diol.

10. A composition according to claim 9, wherein the ligand having activity for a VDR receptor is 1α,25-dihydroxyvitamin D3.

11. A composition according to claim 2, wherein the weight ratio of said at least one ligand which specifically binds to a nuclear receptor of the VDR type to said at least one retinoid which exhibits selective binding affinity for RARγ receptors relative to RARα receptors ranges from 1/1000 to 1000/1.

12. A composition according to claim 11, wherein the weight ratio ranges from 1/10 to 10/1.

13. A composition according to claim 1, which further comprises a pharmaceutically acceptable carrier.

14. A composition according to claim 1, wherein said composition is packaged in a form which is suitable for enteral, parentral, topical or ocular administration.

15. A composition according to claim 2, wherein the ligand which specifically binds to a nuclear receptor of the VDR type is comprised at a concentration ranging from 0.001% to 10% by weight relative to the total weight of the composition.

16. A composition according to claim 1, wherein the retinoid is present at a concentration ranging from 0.001% to 10% by weight relative to the total weight of the composition.

17. The composition of claim 2, wherein said composition comprises an amount of said retinoid which, in the absence of said ligand specific to a nuclear receptor of the VDR type has substantially no effect on the proliferation of skin cells.

18. The composition of claim 17, wherein said retinoid by itself has substantially no effect on the proliferation of keratinocytes.

19. The composition of claim 1, wherein said skin cells comprise keratinocytes.

* * * * *